US008062670B2

(12) United States Patent
Baran, Jr. et al.

(10) Patent No.: US 8,062,670 B2
(45) Date of Patent: Nov. 22, 2011

(54) COMPOSITIONS EXHIBITING IMPROVED FLOWABILITY

(75) Inventors: Jimmie R. Baran, Jr., Prescott, WI (US); Stephen W. Stein, Lino Lakes, MN (US); James S. Stefely, Woodbury, MN (US); Madeline P. Shinbach, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 945 days.

(21) Appl. No.: 11/995,845

(22) PCT Filed: Aug. 4, 2006

(86) PCT No.: PCT/US2006/030278
§ 371 (c)(1),
(2), (4) Date: Jan. 16, 2008

(87) PCT Pub. No.: WO2007/019229
PCT Pub. Date: Feb. 15, 2007

(65) Prior Publication Data
US 2008/0286362 A1    Nov. 20, 2008

Related U.S. Application Data

(60) Provisional application No. 60/705,821, filed on Aug. 5, 2005.

(51) Int. Cl.
*A61K 9/14* (2006.01)
*A61K 9/00* (2006.01)
*A61M 15/00* (2006.01)

(52) U.S. Cl. ........................... 424/489; 424/46; 424/400

(58) Field of Classification Search .................... 424/46, 424/400, 409, 489, 641, 646, 682; 128/200.24
See application file for complete search history.

(56) References Cited

U.S. PATENT DOCUMENTS

| 2,801,185 | A | 7/1957 | Iler |
| 4,455,205 | A | 6/1984 | Olson et al. |
| 4,478,876 | A | 10/1984 | Chung |
| 4,486,504 | A | 12/1984 | Chung |
| 4,491,508 | A | 1/1985 | Olson et al. |
| 4,522,958 | A | 6/1985 | Das et al. |
| 4,767,726 | A | 8/1988 | Marshall |
| 5,037,579 | A | 8/1991 | Matchett |
| 5,254,330 | A | 10/1993 | Ganderton et al. |
| 5,258,225 | A | 11/1993 | Katsamberis |
| 5,883,029 | A | 3/1999 | Castle |
| 6,051,252 | A | 4/2000 | Liebowitz et al. |
| 6,329,058 | B1 | 12/2001 | Arney et al. |
| 6,432,526 | B1 | 8/2002 | Arney et al. |
| 6,585,957 | B1 * | 7/2003 | Adjei et al. ..................... 424/45 |
| 6,586,483 | B2 | 7/2003 | Kolb et al. |
| 7,758,888 | B2 * | 7/2010 | Lapidot et al. ................ 424/489 |
| 2004/0241101 | A1 * | 12/2004 | Baran et al. .................... 424/46 |
| 2006/0251687 | A1 * | 11/2006 | Lapidot et al. ................ 424/401 |

FOREIGN PATENT DOCUMENTS

| CA | 2 203 726 | 10/1997 |
| CN | 1371946 A | 10/2002 |
| DE | 196 16 781 | 11/1997 |

OTHER PUBLICATIONS

Sigma product data sheet for fumed silica accessed on Jan. 25, 2011 at www.sigmaaldrich.com/etc/medialab/docs/Sigma/Product_Information_Sheet/1/s5505pis.Par.0001.File.tmp/s5505pis.pdf.*
Spinhaler photo—accessed on Jan. 26, 2011 at the following URL: www.admit-online.info/en/inhalation-systems/features-of-available-devices/dpi/spinhaler/.*
Hino, Tomoaki, et al. "Particle Design of Dry Powder Inhalers," *Pharm Tech Japan*, vol. 14, No. 10, (1998) p. 1555-1563.
Kawashima, Y., et al., "A New Powder Design Method to Improve Inhalation Efficiency of Pranlukast Hydrate Dry Powder Aerosols by Surface Modification with Hydroxypropylmethylcellulose Phthalate Nanospheres," *Pharmaceutical Research*, vol. 15, No. 11, (1998), p. 1748-1752.
Kawashima, Y., et al., Design of Inhalation Dry Powder of Pranlukast Hydrate to Improve Dispersibility by the Surface Modification with Light Anhydrous Silicic Acid (AEROSIL 200), *International Journal of Pharmaceutics*, vol. 173, (1998), p. 243-251.
Linsenbuhler, Markus, et al., "An Innovative Dry Powder Coating Process in Non-Polar Liquids Producing Tailor-Made Micro-Particles," *Powder Technology*, vol. 158, (2005) p. 3-20.
Article: Carr, Ralph L., "Evaluating Flow Properties of Solids," Chemical Engineering, Jan. 18, 1965, pp. 163-168.
Standard: ASTM D 6393-99, "Standard Test Method for Bulk Solids Characterization by Carr Indices[1]," (1999) pp. 734-740.

* cited by examiner

*Primary Examiner* — James H. Alstrum-Acevedo
(74) *Attorney, Agent, or Firm* — Stephen L. Crooks

(57) ABSTRACT

Powder compositions exhibiting improved flow properties. The compositions generally contain a bulk solid material in the form of a powder and surface-modified nanoparticles. Methods of improving the flow of powder compositions and devices and articles made using such compositions are also disclosed.

27 Claims, No Drawings

COMPOSITIONS EXHIBITING IMPROVED FLOWABILITY

CROSS REFERENCE TO RELATED APPLICATIONS

This application is a national stage filing under 35 U.S.C. 371 of PCT/US2006/030278, filed Aug. 4, 2006, which claims priority to U.S. Patent Application No. 60/705,821, filed Aug. 5, 2005, the disclosure of which is incorporated by reference in its entirety herein.

FIELD

The invention relates generally to compositions of a powder or powder mixture exhibiting substantial ease of flow.

BACKGROUND

The handling, mixing and delivery of bulk solids present unique difficulties when the solids are handled in powdered form. Often, one or more physical properties of the powdered particulates themselves are important, or even critical, to the application for which the composition is intended. Particulate shape, particulate size and particulate porosity often describe important physical properties or characteristics. Environmental conditions (humidity, temperature, shear forces among others) encountered by a powder during use or storage can and often do affect one or more properties of the particulates. Aggregation, agglomeration, attrition and flocculation represent the most common degradative effects on a powder and their presence or progression greatly limits the utility and viability of many powder compositions.

Achieving a uniform blend of dry bulk solids is a problem faced daily by engineers and operators in industries as varied as pharmaceuticals, foods, plastics and battery production. Even when an acceptable blend is obtained additional challenges arise in maintaining the blend through one or more pieces of downstream equipment. Poor blending or the inability to maintain an adequate blend before and during processing lead to additional and unnecessary costs, including costs associated with rejected material and decreased yields, added blending time and energy, decreased productivities, start-up delays and defective or out-of-specification products. Powder caking of raw and in-process materials, particularly during storage (m, e.g., bags or drums) can also pose significant problems. Both powder caking and an inability to achieve uniform blends and mixtures can decrease batch uniformity which, among other drawbacks, can require increased testing and sampling. In pharmaceutical applications, batch nonuniformities translate directly to dose nonuniformities.

Some flowability aids are known. Fumed silica, for example, is one popular powder additive that can be used to improve flow characteristics. While relatively inexpensive, fumed silica often is ineffective in preventing agglomeration of many particle types. Flowability is also a matter of degree; many, if not most, uses of fumed silica lead to some agglomeration and aggregation. Some undemanding industrial applications can tolerate a level of agglomeration not tolerated in more demanding applications. Applications involving precise metering or mixing of a powder, however, require more. Even in relatively undemanding applications the ability to improve powder flow can provide an increase in homogeneity with milder mixing conditions or with reduced mixing periods. Additionally, increased powder flowabilities can allow utilization of lower levels of expensive ingredients, e.g., dyes and pigments, particularly where the requirement of using a level of such ingredients correlates with the dispersibility of the materials in the powder with which they are mixed.

The preparation or delivery of pharmaceuticals and medicaments as powders is particularly demanding. Pharmaceutical applications must take careful account of various particle or powder characteristics, and pharmaceutical compositions often are prepared as powders as an intermediate step to final formulation in myriad forms for delivery to the patient. Pharmaceutical compositions can be tableted or encapsulated for oral gastro-intestinal ingestion and delivery. They also can be incorporated into a dry powder inhaler for delivery to the respiratory tract. The ability to achieve homogenous blends of compositions containing relatively low levels (by weight) of pharmaceutically active ingredients is very difficult.

Dry powder inhalation of a pharmaceutical or drug composition requires unique and challenging physical property profiles for a powder. In order to efficiently and efficaciously deliver pharmaceutical compositions to the lung in powdered form two competing criteria must be balanced:

1. The drug particles to be delivered must be sufficiently small so that the particles can be inhaled and penetrate into the deep lung. The aerodynamic diameter of the particles (Equation 1 below) primarily influences this behavior, since deposition in the respiratory tract is controlled by a particle's aerodynamic size rather than its physical or geometric shape. Lung deposition improves substantially for particles less than 5 microns in aerodynamic diameter and decreases substantially for particles with effective aerodynamic diameters of greater than 5 microns.

$$D_{aerodynamic} \cong D_{physical}\sqrt{\frac{\rho}{\chi}} \quad (1)$$

where: $\rho$ is the particle density; and
$\chi$ is the shape factor of the particle ($\chi=1.0$ for perfectly spherical particles and $\chi \geq 1$ for irregular particles)

2. Drug particles need also to be sufficiently deagglomerated by a dry powder inhaler ("DPI") device. Large clusters of multiple drug particles will not penetrate into the deep lung as efficiently as single or very small particle clusters. Traditionally, DPIs have utilized complex mechanical systems to ensure deagglomeration of the particulate powder and even then such systems have yielded only partial success. Competing with the desire for decreasing particle size, the flowability and ease of deagglomeration of powders unfortunately improves with increasing particle size. Below 5 microns in effective particle diameter deagglomeration efficiency exhibits a marked decline.

To balance these competing effects, recent efforts have developed powders for inhalation that are physically large (and thus effectively deagglomerated), yet are aerodynamically small (thus being more respirable). Some such particles, for example, are hollow spherical-like particles with low density but large relative particle size. Others are significantly irregular in shape and physical character. While achieving some degree of balance between penetrability and flowability, powders of such particles, particularly when formulated in lipid/drug matrices for delivery, tend toward an amorphous state and pose potential stability drawbacks. Concerns also arise when inhaling a large amount of the excipients required to form such matrices. Other methods to balance the competing effects have included adsorbing small respirable drug particles onto larger inert particles (e.g., lactose) which act as a carrier for the particles to provide for bulk deagglomeration but which require additional energy to release the drug from the surface of the carrier particle. Such an approach limits the amount of drug that can be delivered, since a substantial amount of the formulation is comprised of pharmaceutically non-active ingredients. Additional concerns surround the preparation of such powders in a homogenous manner and the ability to measure precise amounts of the powder blends in the final delivery vehicles.

Powder handling and processing technologies today lie significantly behind the development pace of companion technologies used in liquid processes, and there remain a great many practical problems handling powders that current methods cannot effectively address. Powder compositions exhibiting enhanced flowability and processability are desired for a wide range of applications including demanding industrial and pharmaceutical uses.

SUMMARY

In one aspect, the present invention provides powder compositions exhibiting improved flowability and ease of mixing. Such compositions comprise at least one bulk solid phase in the form of a powder and at least an effective amount of a flow enhancing agent comprising surface-modified nanoparticles. The compositions can exhibit substantially free flowing characteristics and substantially increased packing densities compared with compositions that do not include the flow enhancing agent.

In another aspect the invention provides compositions comprising at least one bulk solid material substantially in the form of a powder and surface-modified nanoparticles. The surface-modified nanoparticles are present in the compositions in an amount that is at least sufficient to improve the flowability or floodability of the bulk solid material relative to the bulk solid material substantially free of surface-modified nanoparticles.

In another aspect, the invention provides pharmaceutical compositions exhibiting substantially improved flow characteristics. Such pharmaceutical compositions comprise at least one solid phase including one or more medicaments and an effective amount of at least one surface-modified nanoparticle.

In another aspect, the present invention provides pharmaceutical compositions that exhibit substantially improved flow characteristics, where the flowability is improved by at least 5 percent. The compositions comprise at least one solid phase including one or more medicaments and an effective amount of at least one biocompatible surface-modified nanoparticle. The biocompatible particles may be biodegradable or bioadsorbable or may be inert and excreted intact as may be desirably for the selection route or method of biological exposure.

In other aspects, the invention provides methods of mixing and dry blending solid compositions comprising mixing or blending one or more solid phase powders with a flow enhancing agent that contains an effective amount of at least one surface-modified nanoparticle.

In still other aspects, the invention provides substantially free flowing powder mixtures comprising one or more powder compositions and an effective amount of at least one surface-modified nanoparticle.

In yet other aspects, the invention provides methods of making substantially free-flowing powder compositions, methods of using such compositions and devices incorporating such compositions.

DETAILED DESCRIPTION

The compositions of the invention include a flow enhancing material comprising surface-modified nanoparticles. In an exemplary embodiment, the surface-modified nanoparticles are individual, unassociated (i.e., non-aggregated) particles that are mixed with, blended with or are otherwise distributed within a bulk solid material which is in powder form. While not subject to any specific physical characterization and not intending to be limited to any single characterization, one non-limiting way to identify a solid material as a powder is when it is composed principally of relatively small individual particles or relatively small groups of individual particles. Generally, such particles will have an average size (generally measured as an effective diameter) of less than or equal to 1,000 microns, more typically less than or equal to 100 microns. The bulk solid powder material may be distinguished from the nanoparticles by relative size, wherein the bulk solid powder material comprises particles that are larger than the nanoparticles. The term "nanoparticle" as used herein (unless an individual context specifically implies otherwise) will generally refer to particles, groups of particles, particulate molecules such as small individual groups or loosely associated groups of molecules, and groups of particulate molecules that while potentially varied in specific geometric shape have an effective, or average, diameter that can be measured on a nanoscale (less than 100 nanometers).

The nanoparticles utilized in the invention enhance and/or maintain the flowability of the bulk powder materials within which they are present. Flowability (also called free flow) refers generally to the ability of a free-flowing material to flow steadily and consistently as individual particles or groups of individual particles such as would occur, for example, through a fine orifice. The presence of nanoparticles in the compositions of the invention also enhance floodability (also called floodable flow), which refers to the tendency of a solid or powder material toward liquid-like flow due to the material fluidization of a mass of particles by a gaseous carrier. There can be several different ways to characterize the flowability or floodability of a powder. The surface-modified nanoparticles, when present in a powder composition in accordance with the present invention, will provide an improvement in flowability and/or floodability of the powder composition when compared to the flowability and/or floodability of the bulk powder composition when substantially free of the nanoparticles. Substantially free refers essentially to the lack or presence of a component, such as nanoparticles in the bulk powder composition. Such an improvement may be evidenced by at least one of the following of Examples 11-20: (1) an increase in the tap density of the powder composition, preferably by a factor of at least 1.25 or more, preferably by a factor of at least 2.0; (2) a decrease in the angle of repose of the powder composition; (3) an increase in the Flowability Index of the powder composition; or (4) an increase in the Floodability Index of the powder composition. Also, the inclusion of surface-modified nanoparticles allow for higher tap densities, where a larger concentration of a medicament may be contained in a capsule, a blister, or a reservoir-based DPI device. For example, this may contribute to more doses in a DPI device within the same sized device, rather than changing the device's shape or size. It will be understood, however, that other measurements can also be used to demonstrate improved powder flowabilities. An improvement in powder flowability can, for example, be inferred by relative improvement as compared to compositions substantially free of the nanoparticle compositions utilized in the invention in phenomena and process parameters that are correlated with flowability. Relative improvements such as reductions in aggregation, agglomeration, attrition, flocculation, segregation, caking, bridging or in the ability to achieve uniform blends will all be understood to reflect an improvement in flowability as herein defined.

In one exemplary embodiment, a class of surface-modified nanoparticles utilized in the invention are comprised of a core material and a surface that is different or modified from the core material. The core material may be inorganic or organic and is selected such that, as described in more detail herein, it is compatible with the bulk solid material with which it is combined and it is suitable for the application for which it is intended. Generally the selection of the core material will be governed at least in part by the specific performance requirements for the composition and any more general requirements for the intended application. For example, the performance requirements for the solid composition might require that a given core material have certain dimensional characteristics (size and shape), compatibility with the surface modifying materials along with certain stability requirements (insolubility in a processing or mixing solvent). Other requirements might be prescribed by the intended use or application of the solid composition. Such requirements might include, for example, biocompatibility or stability under more extreme environments, such as high temperatures.

Suitable inorganic nanoparticle core materials include calcium phosphate, hydroxyapatite, and metal oxide nanoparticles such as zirconia, titania, silica, ceria, alumina, iron oxide, vanadia, zinc oxide, antimony oxide, tin oxide, alumina/silica, and combinations thereof. Metals such as gold, silver, or other precious metals can also be utilized as solid particles or as coatings on organic or inorganic particles.

Suitable organic nanoparticle core materials include, for example, organic polymeric nanospheres, insoluble sugars such as lactose, trehalose, glucose or sucrose, and insoluble aminoacids. In another embodiment, another class of organic polymeric nanospheres includes nanospheres that comprise polystyrene, such as those available from Bangs Laboratories, Inc. of Fishers, Ind. as powders or dispersions. Such organic polymeric nanospheres will generally have average particle sizes ranging from 20 nm to not more than 60 nm.

It will be understood that the selected nanoparticle core material may be used alone or in combination with one or more other nanoparticle core materials including mixtures and combinations of organic and inorganic nanoparticle materials. Such combinations may be uniform or have distinct phases, which can be dispersed or regionally specific, such as layered or of a core-shell type structure. The selected nanoparticle core material, whether inorganic or organic, and in whatever form employed, will generally have an average particle diameter of less than 100 nm. In some embodiments, nanoparticles may be utilized having a smaller average effective particle diameter of, for example less than or equal to 50, 40, 30, 20, 15, 10 or 5 nm; in some embodiments from 2 nm to 20 nm; in still other embodiments from 3 nm to 10 nm. If the chosen nanoparticle or combination of nanoparticles are themselves aggregated, the maximum preferred cross-sectional dimension of the aggregated particles will be within any of these stated ranges.

In an exemplary embodiment, another class of surface-modified organic nanoparticles includes buckminsterfullerenes (fullerenes), dendrimers, branched and hyper-branched "star" polymers such as 4, 6, or 8 armed polyethylene oxide (available, for example, from Aldrich Chemical Company of Milwaukee, Wis. or Shearwater Corporation of Huntsville, Ala.) whose surface has been chemically modified. Specific examples of fullerenes include $C_{60}$, $C_{70}$, $C_{82}$, and $C_{84}$. Specific examples of dendrimers include polyamidoamine (PAMAM) dendrimers of Generations 2 through 10 (G2-G10), available also from, for example, Aldrich Chemical Company of Milwaukee, Wis.

In many cases it may be desirable for the nanoparticles utilized in the invention to be substantially spherical in shape. In other application, however, more elongated shapes by be desired. Aspect ratios less than or equal to 10 are considered preferred, with aspect ratios less than or equal to 3 generally more preferred. The core material will substantially determine the final morphology of the particle and thus a significant influence in selection of the core material may be the ability to obtain a desired size and shape in the final particle.

The surface of the selected nanoparticle core material will generally be chemically or physically modified in some manner. Both direct modification of a core surface as well as modification of a permanent or temporary shell on a core material are envisioned. Such modifications may include, for example, covalent chemical bonding, hydrogen bonding, electrostatic attraction, London forces and hydrophilic or hydrophobic interactions so long as the interaction is maintained at least during the time period required for the nanoparticles to achieve their intended utility. The surface of a nanoparticle core material may be modified with one or more surface modifying groups. The surface modifying groups may be derived from myriad surface modifying agents. Schematically, surface modifying agents may be represented by the following general formula:

$$A-B \quad \quad \quad (II)$$

The A group in Formula II is a group or moiety that is capable of attaching to the surface of the nanoparticle. In those situations where the nanoparticle and/or bulk powder material is processed in solvent, the B group is a compatibilizing group with whatever solvent is used to process the nanoparticle and the bulk powder materials. In those situations where the nanoparticles and/or bulk powder materials are not processed in solvent, the B group is a group or moiety that is capable of preventing irreversible agglomeration of the nanoparticle. It is possible for the A and B components to be the same, where the attaching group may also be capable of providing the desired surface compatibility. The compatibilizing group may be reactive, but is generally non-reactive, with a component of the bulk powder phase. It is understood that the attaching composition may be comprised of more than one component or created in more than one step, e.g., the A composition may be comprised of an A' moiety which is reacted with the surface, followed by an A" moiety which can then be reacted with B. The sequence of addition is not important, i.e., the A'A"B component reactions can be wholly or partly performed prior to attachment to the core. Further description of nanoparticles in coatings can be found in Linsenbuhler, M. et. al., *Powder Technology*, 158, 2003, p. 3-20.

Many suitable classes of surface-modifying agents are known to those skilled in the art and include, for example, silanes, organic acids, organic bases and alcohols, and combinations thereof.

In another embodiment, surface-modifying agents include silanes. Examples of silanes include organosilanes such as, for example, alkylchlorosilanes; alkoxysilanes, e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, isooctyltrimethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris(isopropenoxy)silane, and vinyltris(2-methoxyethoxy)silane; trialkoxyarylsilanes; isooctyltrimethoxysilane; N-(3-triethoxysilylpropyl)methoxyethoxyethyl carbamate; N-(3-triethoxysilylpropyl)methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane, and 3-(methacryloyloxy)propyltrimethoxysilane; polydialkylsiloxanes including, e.g., polydimethylsiloxane; arylsilanes including, e.g., substituted and unsubstituted arylsilanes; alkylsilanes including, e.g., substituted and unsubstituted alkyl silanes including, e.g., methoxy and hydroxy substituted alkyl silanes, and combinations thereof.

Methods of surface-modifying silica using silane functional (meth)acrylates are known and are described, for example, in U.S. Pat. Nos. 4,491,508 (Olson et al.); 4,455,205 (Olson et al.); 4,478,876 (Chung); 4,486,504 (Chung); and 5,258,225 (Katsamberis) whose descriptions are incorporated herein by reference for such purpose. Surface-modified silica nanoparticles include silica nanoparticles surface-modified with silane surface modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, e.g., alcohol, organosilane including, e.g., alkyltrichlorosilanes, trialkoxyarylsilanes, trialkoxy(alkyl)silanes, and combinations thereof and organotitanates and mixtures thereof.

In another embodiment, organic acid surface-modifying agents include, for example, oxyacids of carbon (e.g., carboxylic acid), sulfur and phosphorus, acid derivatized poly (ethylene) glycols (PEGs) and combinations of any of these. Suitable phosphorus containing acids include phosphonic acids including, e.g., octylphosphonic acid, laurylphosphonic acid, decylphosphonic acid, dodecylphosphonic acid, octadecylphosphonic acid, monopolyethylene glycol phosphonate and phosphates including lauryl or stearyl phosphate. Suitable sulfur containing acids include sulfates and sulfonic acids including dodecyl sulfate and lauryl sulfonate. Any such acids may be used in either acid or salt forms.

Non-silane surface modifying agents include acrylic acid, methacrylic acid, beta-carboxyethyl acrylate, mono-2-(methacryloyloxyethyl) succinate, mono(methacryloyloxypolyethyleneglycol) succinate and combinations of one or more of such agents. In another embodiment, surface-modifying agents incorporate a carboxylic acid functionality such as, for example, $CH_3$—O—$(CH_2CH_2O)_2CH_2COOH$ (hereafter, MEEAA), 2-(2-methoxyethoxy)acetic acid having the chemical structure $CH_3OCH_2CH_2OCH_2COOH$ (hereafter MEAA), mono(polyethylene glycol) succinate in either acid or salt form, octanoic acid, dodecanoic acid, steric acid, acrylic and oleic acid or their acidic derivatives. In a further embodiment, surface-modified iron oxide nanoparticles include those modified with endogenous fatty acids, e.g., steric acid, or fatty acid derivatives using endogenous compounds, e.g., steroyl lactylate or sarcosing or taurine derivatives. Further surface-modified zirconia nanoparticles include a combination of oleic acid and acrylic acid adsorbed onto the surface of the particle.

Organic base surface-modifying agents may also include alkylamines, e.g., octylamine, decylamine, dodecylamine, octadecylamine, and monopolyethylene glycol amines. Other non-silane surface modifying agents include acrylic acid, methacrylic acid, beta-carboxyethyl acrylate, mono-2-(methacryloyloxyethyl) succinate, mono(methacryloyloxypolyethyleneglycol) succinate and combinations of one or more of such agents.

Surface-modifying alcohols and thiols may also be employed including, for example, aliphatic alcohols, e.g., octadecyl, dodecyl, lauryl and furfuryl alcohol, alicyclic alcohols, e.g., cyclohexanol, and aromatic alcohols, e.g., phenol and benzyl alcohol, and combinations thereof. Thiol-based compounds are especially suitable for modifying cores with gold surfaces.

The surface-modified nanoparticles are selected in such a way that compositions formed with them are free from a degree of particle agglomeration or aggregation that would interfere with the desired properties of the composition. The surface-modified nanoparticles are generally selected to be either hydrophobic or hydrophilic such that, depending on the character of the processing solvent or the bulk material, the resulting mixture or blend exhibits substantially free flowing properties.

Suitable surface groups constituting the surface modification of the utilized nanoparticles can thus be selected based upon the nature of the processing solvents and bulk materials used and the properties desired of the resultant combination. When a processing solvent is hydrophobic, for example, one skilled in the art can select from among various hydrophobic surface groups to achieve a surface-modified particle that is compatible with the hydrophobic solvent; when the processing solvent is hydrophilic, one skilled in the art can select from various hydrophilic surface groups; and, when the solvent is a hydrofluorocarbon or fluorocarbon, one skilled in the art can select from among various compatible surface groups; and so forth. The nature of the bulk material and the desired final properties can also affect the selection of the surface composition. The nanoparticle can include two or more different surface groups (e.g., a combination of hydrophilic and hydrophobic groups) that combine to provide a nanoparticle having a desired set of characteristic. The surface groups will generally be selected to provide a statistically averaged, randomly surface-modified particle.

The surface groups will be present on the surface of the particle in an amount sufficient to provide surface-modified nanoparticles with the properties necessary for compatibility with the bulk material. In an exemplary embodiment, the surface groups are present in an amount sufficient to form a monolayer, and in another embodiment, a continuous monolayer, on the surface of at least a substantial portion of the nanoparticle.

A variety of methods are available for modifying the surfaces of nanoparticles. A surface modifying agent may, for example, be added to nanoparticles (e.g., in the form of a powder or a colloidal dispersion) and the surface modifying agent may be allowed to react with the nanoparticles. One skilled in the art will recognize that multiple synthetic sequences to bring the nanoparticle together with the compatibilizing group are possible and are envisioned within the scope of the present invention. For example, the reactive group/linker may be reacted with the nanoparticle followed by reaction with the compatibilizing group. Alternatively, the reactive group/linker may be reacted with the compatibilizing group followed by reaction with the nanoparticle. Other surface modification processes are described in, e.g., U.S. Pat. Nos. 2,801,185 (Iler) and 4,522,958 (Das et al.), whose descriptions are incorporated herein by reference for such purpose.

Surface-modified nanoparticles or precursors to them may be in the form of a colloidal dispersion. Some such dispersions are commercially available as unmodified silica starting materials, for example those nano-sized colloidal silicas available under the product designations NALCO 1040, 1050, 1060, 2326, 2327, and 2329 colloidal silica from Nalco Chemical Co. of Naperville, Ill. Metal oxide colloidal dispersions include colloidal zirconium oxide, suitable examples of which are described in U.S. Pat. No. 5,037,579 (Matchett) (whose description is incorporated by reference herein), and colloidal titanium oxide, examples of which are described in U.S. Pat. Nos. 6,329,058 and 6,432,526 (Arney et al.), whose descriptions are also incorporated by reference herein. Such particles are also suitable substrates for further surface modification as described above.

The bulk powder phase (i.e., the bulk solid material) may contain any one or mixture of particles for which a desired degree of flowability is desired. Generally, the bulk phase particulate powders will have median particle size diameters less than 200 micrometers, but greater than 100 μm. In some instances, the bulk phase particulate powders may have median particle size diameters less than 100 nm in size, but larger than the surface-modified nanoparticles. In one embodiment, the bulk phase particulate powders will have median particle size diameters ranging from 0.5 micrometer to 200 micrometers, preferably from 1 micrometer to 200 micrometers, and more preferably from 1 micrometer to 100 micrometers. The bulk phase particulate powders may be inorganic, organic or any combination thereof. Examples of bulk phase powders include polymers; medicaments; pigments; abrasives; additives; ceramic (e.g., glass, crystalline ceramic, glass-ceramic, and combinations thereof) bubbles; ceramic microspheres; silicates (e.g., talc, clay, sericite); fillers such as carbon black, titanium dioxide, calcium carbonate, nepheline ("MINEX", Unimin Corp, New Canaan, Conn.), Feldspar and Wollastonite; excipients such as microcrystalline cellulose (and other natural or synthetic polymers), dicalcium phosphate, lactose monohydrate and other sugars; exfoliants; cosmetic ingredients; aerogels; foodstuffs; glass materials and toner materials.

Suitable ceramic bubbles and ceramic microspheres are exemplified in U.S. Pat. Nos. 4,767,726 (Marshall), and 5,883,029 (Castle), herein incorporated by reference.

Examples of commercially available glass bubbles include those marketed by 3M Company under the trade designation "3M™ SCOTCHLITE GLASS BUBBLES" (e.g., grades K1, K15, S15, S22, K20, K25, S32, K37, S38, K46, S60/10000, S60HS, A16/500, A20/1000, A20/1000, A20/1000, A20/1000, H50/10000 EPX, and H50/10000 (acid washed)); glass bubbles marketed by Potter Industries, Valley Forge, Pa., under the trade designation "SPHERICEL" (e.g., grades 110P8 and 60P18), "LUXSIL", and "Q-CEL" (e.g., grades 30, 6014, 6019, 6028, 6036, 6042, 6048, 5019, 5023, and 5028); hollow glass microspheres marketed under the trade designation "DICAPERL" by Grefco Minerals, Bala Cynwyd, Pa., (e.g., grades HP-820, HP-720, HP-520, HP-220, HP-120, HP-900, HP-920, CS-10-400, CS-10-200, CS-10-125, CSM-10-300, and CSM-10-150); and hollow glass particles marketed by Silbrico Corp., Hodgkins, Ill., under the trade designation "SIL-CELL" (e.g., grades SIL 35/34, SIL-32, SIL-42, and SIL-43).

Examples of commercially available ceramic microspheres include ceramic hollow microspheres marketed by SphereOne, Inc. under the trade designation, "EXTENDOSPHERES" (e.g., grades SG, CG, TG, SF-10, SF-12, SF-14, SLG, SL-90, SL-150, and XOL-200); and ceramic microspheres marketed by 3M Company under the trade designation "33M Ceramic Microspheres" (e.g., grades G-200, G-400, G-600, G-800, G-850, W-210, W-410, and W-610).

Surface-modified nanoparticles are present in the bulk solid materials utilized in the invention (which may comprise a mixture of one or more bulk materials) in an amount effective to enhance the flowability or floodability of the bulk material by reducing or minimizing the degree of aggregation, agglomeration or flocculation of the bulk material. The amount of surface-modified nanoparticle effective to achieve this purpose will depend, inter alia, on the composition of the bulk material, the chosen nanoparticle, the presence or absence of other adjuvants or excipients and on the particular needs and requirements of the application for which the bulk material is to be used. For example, the nature of the nanoparticle surface, the morphology of the particle and particle size may each influence the desired properties of the composition and influence the selection of a nanoparticle and the amount or concentration of nanoparticle used. The presence of as little as 0.001 percent of nanoparticle by weight of the combined composition can achieve an improvement in flowability. Generally, the nanoparticle will be present in an amount of less than or equal to 10 weight percent; in some embodiments less than or equal to 5 weight percent; less than or equal to 1 weight percent; or less than 0.1 weight percent. In some embodiments, the amount of surface-modified nanoparticles is from 0.001 to 20 percent; from 0.001 to 10 percent; from 0.001 to 1 percent; from 0.001 to 0.01 percent; or from 0.01 to 1 percent, by weight of the composition. In many applications it may be preferred that the selected nanoparticles be substantially spherical. The toxicology and biocompatibility of a selected nanoparticle will be particularly relevant and important for pharmaceutical applications. It will be understood that such selection and optimization of component compositions will be within the skill of those in the art who are familiar with the physical properties required for the composition in a given use or application.

In one exemplary embodiment, the surface-modified nanoparticles will not irreversibly associate with one another. The term "associate with" or "associating with" includes, for example, covalent bonding, hydrogen bonding, electrostatic attraction, London forces, and hydrophobic interactions.

One application of the invention involves uses to enhance the mixing and/or delivery of medicament compositions. Medicaments include antiallergics, analgesics, bronchodilators, antihistamines, therapeutic proteins and peptides, antitussives, anginal preparations, antibiotics, anti-inflammatory preparations, diuretics, hormones, or sulfonamides, such as, for example, a vasoconstrictive amine, an enzyme, an alkaloid or a steroid, and combinations of any one or more of these. Noted categories include beta-agonists, bronchodilators, anticholinergics, anti-leukotrienes, mediator release inhibitors, 5-lipoxyoxygenase inhibitors, and phosphodiesterase inhibitors. Specific exemplary medicaments include the following: isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol, isoprenaline, fenoterol, oxitropium bromide, reproterol, budesonide, flunisolide, ciclesonide, formoterol, fluticasone propionate, salmeterol, procaterol, ipratropium, triamcinolone acetonide, tipredane, mometasone furoate, colchicine, pirbuterol, beclomethasone, beclomethasone dipropionate, orciprenaline, fentanyl, diamorphine, and diltiazem. Others are antibiotics, such as neomycin, cephalosporins, streptomycin, penicillin, procaine penicillin, tetracycline, chlorotetracycline and hydroxytetracycline; adrenocorticotropic hormone and adrenocortical hormones, such as cortisone, hydrocortisone, hydrocortisone acetate and prednisolone; antiallergy compounds such as cromolyn sodium, nedocromil protein and peptide molecules such as insulin, pentamidine, calcitonin, amiloride, interferon, LHRH analogues, IDNAase, heparin, and others.

If appropriate for a specific application the medicaments may be used as either a free base or as one or more salts known to the art. The choice of a free base or salt will be influenced by the biological impact as well as the chemical and physical stability (e.g., its tendency toward solvates, multiple polymorphs, friability, etc.) of the medicament in a given formulation. Among salts of medicaments in the present invention are the following: acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphatediphosphate, polygalacturonate, salicylate, stearate, subacetate, succinate, sulphate, tannate, tartrate, and triethiodide.

Cationic salts of a medicament may also be used. Suitable cationic salts include the alkali metals, e.g., sodium and potassium, and ammonium salts and salts of amines known in the art to be pharmaceutically acceptable, e.g., glycine, ethylene diamine, choline, diethanolamine, triethanolamine, octadecylamine, diethylamine, triethylamine, 1-amino-2-propanol-amino-2-(hydroxymethyl)propane-1,3-diol and 1-(3,4-dihydroxyphenyl)-2 isopropylaminoethanol.

For pharmaceutical purposes, the particle size of a medicament powder will generally be no greater than 100 micrometers in diameter. In other embodiments, the particle size will be less than 25 micrometers in diameter. Desirably, the particle size of the finely-divided solid powder should for physiological reasons be less than 25 micrometers in diameter and in other embodiments, less than 10 micrometers in diameter, and in other embodiments, less than 5 micrometers.

Pharmaceutical formulations frequently will consist of blends of one or more medicaments with one or more excipients that are used as intermediate materials (isolated or in-process) before the final product is manufactured. Suitable excipients are listed in the Handbook of Pharmaceutical Excipients (Rowe, et al., APhA Publications, 2003) and are exemplified by microcrystalline cellulose, dicalcium phosphate, lactose monohydrate, mannose, sorbitol, calcium carbonate, starches and magnesium or zinc stearates. The surface-modified nanoparticles may have many potential benefits in the preparation of these excipients/medicament blends, including reducing mixing times, reducing attrition during processing and improving the homogeneity of the blend.

In another use, a pharmaceutical inhalation powder formulation will consist of a medicament, an optional excipient, and surface-modified nanoparticles. It may be desirable for the medicament particles to be less than 10 micrometers in size such that they can be inhaled into the lung of a patient. The optional excipient may consist of a sugar, such as lactose monohydrate, and may have particle sizes substantially larger than 10 microns. The surface-modified nanoparticles may be configured in such a way that they are arranged on the surface of the medicament and/or optional excipient particles. In one embodiment, the surface-modified nanoparticles may be primarily contained on the surface of large excipient particles, such that when the patient inhales the formulation, a substantial fraction of the respirable medicament particles deposit in the patient's lung, whereas the large excipient particles, and the nanoparticles on the surface of the large excipient particles collect in the patient's mouth and throat. In this way, the amount of nanoparticles reaching the patient's lung may be minimized.

In another embodiment, the dry power inhalers may have the powder stored in a storage device prior to dosing. This storage device may comprise a reservoir, capsule, blister, or dimpled tape. In an exemplary embodiment, the drug powder used in the formulation is a micronized crystalline powder, but may also be an amorphous powder from a process such as spray drying. Additionally, the drug may be contained in particles that are a matrix of drug and some excipient. The DPI may be a multi-dose device or may be a single dose device.

A further embodiment of this invention is a method to decrease the flow rate sensitivity of dry powder inhaler drug delivery. Delivery from DPIs often is highly dependent on the flow rate through the inhaler. When the powder formulations of this invention are used in dry powder inhalers, particularly passive dry powder inhalers, the flow rate sensitivity of the drug delivery from the DPIs is reduced. In an exemplary embodiment, the DPIs described may be used for delivery to patients who are unable to achieve a high respiratory flow rate, i.e., asthmatics, elderly, and young children.

In a further embodiment, the pharmaceutical powder formulation may be used for nasal drug delivery.

The compositions of the invention will find utility in any application where an increase or improvement in flow properties of a powder material is desired. Some specific applications, including those outside pharmaceutical applications, for the compositions and methods of the invention include:

(a) In the weighing, metering and mixing of powders where accurate measurements and or increased homogeneities are required;
(b) In any application where an increase in powder "tap density" (decreased volume per unit mass) is desired, including as an aid to the shipment or storage of bulk materials in powder form;
(c) In the preparation of solid ink jet or printing inks and toners;
(d) In the preparation, handling and mixing of paint pigments;
(e) To increase graphite densities in battery anodes;
(f) To decrease the amount of energy required to mix or blend powders;
(g) To prepare passive dry powder inhalers, wherein the inhaler relies on the patient's inspiratory airflow to aerosolize and/or deagglomerate the powder;
(h) To prepare dry powder inhaler (DPI) devices with one or more pharmaceutically active materials. DPI devices contain a mouthpiece and a powder containment system. Compositions of the invention that comprise a bulk solid material (that includes one or more pharmaceutically active ingredients) and nanoparticles may be placed in the powder containment system;

(i) To improve the accuracy and/or homogeneity of pharmaceutical compositions that are filled into capsules or formed into tablets; and (j) To prepare high tap density powders for use in rapid dissolve tablets, such as described in U.S. Pat. No. 6,051,252 (Liebowitz et al.), herein incorporated by reference.

Compositions of the present invention will generally be prepared by mixing the bulk powder material with the surface-modified nanoparticles using any suitable, conventional mixing or blending process. In one embodiment, as illustrated in the Examples below, the surface-modified nanoparticle is prepared as a dispersion in an organic solvent and the bulk powder material is added to the dispersion. Typical solvents that may be employed include, for example, toluene, isopropanol, heptane, hexane, and octane.

In another embodiment of the disclosure, the surface-modified nanoparticles and the bulk powder material are blended as powders, e.g., dry blended.

The following examples are offered to aid in the understanding of the present invention and are not to be construed as limiting the scope thereof. Unless otherwise indicated, all parts and percentages are by weight.

EXAMPLES

Unless otherwise noted, all reagents and solvents were or can be obtained from Aldrich Chemical Co., Milwaukee, Wis.

Surface-modified silica nanoparticles, modified with isooctyltrimethoxysilane ('isooctyl'), methyltrimethoxysilane ('methyl'), or octadecyltrimethoxysilane ('octadecyl') groups, were prepared using the method described in U.S. Pat. No. 6,586,483, which is incorporated herein by reference for such purpose. NALCO 2326 colloidal silica was used as the core for 5 nm size particles and NALCO 2327 was used as the core for 20 nm size particles.

Examples 1-9 and Comparative Examples 1-3

The dry powders (500 g in each of Examples 1-9) were combined with a suspension of the nanoparticles in toluene to provide a mixture in which the dry weight percentage of nanoparticles was 0.01, 0.1, 0.5, or 1.0. Measured aliquots of a 1 weight percent dispersion of the surface-modified nanoparticles in toluene were combined with additional toluene to make 500 g of dispersion containing a sufficient mass of surface-modified nanoparticles to prepare each desired mixture with each of the powders. Each mixture was thoroughly combined using a Silverson Model L4R (Silverson Machines, Inc., East Longmeadow, Mass.) homogenizer for 30 minutes. Each mixture was then dried overnight in a forced air oven at 150° C. The composition of each mixture is given in Table 1. In each Comparative Example, no surface-modified nanoparticles were combined with the powders; the powders were combined with toluene and were mixed and dried as described above. In each Comparative Example in Table 1, " - - - " indicates "none," i.e., that no surface modified nanoparticles were combined with the powders. In Example 10, the albuterol sulfate powder was added to isopropanol to make a 1 weight percent dispersion. This dispersion was combined with a 1 weight percent dispersion of the surface-modified nanoparticles in isopropanol. The mixture was spray dried to afford a dry powder.

TABLE 1

Examples 1-10 and Comparative Examples 1-3

| Example | Nanoparticle Size | Surface Modification | Wt % Nanoparticles | Powder |
|---|---|---|---|---|
| 1 | 5 nm | isooctyl | 1% | Lactose |
| Comparative 1 | — | — | — | Lactose |
| 2 | 5 nm | isooctyl | 1% | 5 micron CaCO$_3$ |
| Comparative 2 | — | — | — | 5 micron CaCO$_3$ |
| 3 | 5 nm | isooctyl | 1% | 10 micron CaCO$_3$ |
| Comparative 3 | — | — | — | 10 micron CaCO$_3$ |
| 4 | 5 nm | isooctyl | 0.5% | 10 micron CaCO$_3$ |
| 5 | 5 nm | isooctyl | 0.1% | 10 micron CaCO$_3$ |
| 6 | 5 nm | isooctyl | 0.01% | 10 micron CaCO$_3$ |
| 7 | 5 nm | octadecyl | 1% | 10 micron CaCO$_3$ |
| 8 | 20 nm | isooctyl | 1% | 10 micron CaCO$_3$ |
| 9 | 20 nm | octadecyl | 1% | 10 micron CaCO$_3$ |
| 10 | 5 nm | isooctyl | 1% | albuterol sulfate |

The powder mixtures were characterized using the standard test method described in ASTM D6393-99 ("Standard Test Method for Bulk Solids Characterization by Carry Indices") using a Model PT-N powder characteristics tester (available from Hosokawa Micron Powder Systems, Summit, N.J.). The Carr Indices were derived after the methods described by Carr in Chemical Engineering vol. 72, pp. 163-168 (1965). The data are given in Tables 2 and 3. The angles of repose, fall, spatula, and difference are reported in units of degrees. The bulk densities are reported in units of grams per cubic centimeter. Compressibility, cohesiveness, and dispersibility are reported as percentages. In Table 2, "CE" refers to Comparative Examples.

TABLE 2

Examples 11-13 and Comparative Examples 4-6

| | Example | | | | | |
|---|---|---|---|---|---|---|
| | 11 | CE4 | 12 | CE5 | 13 | CE6 |
| Powder from Example | 1 | CE1 | 2 | CE2 | 3 | CE3 |
| Angle of Repose (Index) | 32.9 (21) | 47.3 (12) | 32.1 (21) | 43.6 (16) | 23.2 (25) | 55.6 (9.5) |
| Angle of Fall (Index) | 14.1 (24) | 27.4 (18) | 15.4 (24) | 42.2 (12) | 13 (24) | 42.7 (12) |
| Angle of Difference (Index) | 18.8 (17.5) | 19.9 (18) | 16.7 (16) | 1.2 (3) | 10.2 (10) | 12.9 (12) |
| Loose Bulk Density | 0.768 | 0.542 | 0.636 | 0.265 | 0.855 | 0.291 |
| Packed Bulk Density | 1.018 | 0.949 | 1.123 | 0.789 | 1.199 | 0.797 |
| Compressibility (Index) | 24.5 (15) | 42.8 (2) | 43.3 (2) | 66.4 (0) | 28.6 (12) | 63.4 (0) |
| Cohesiveness (Index) | 40.8 (7) | 21.6 (12) | 19.6 (12 | 99.5 (0)) | 18.8 (12) | 89.1 (0) |
| Angle of Spatula (Index) | 63 (12) | 64.1 (12) | 70.1 (12) | 89.6 (5) | 58.1 (16) | 69.7 (12) |
| Dispersibility (Index) | 47.1 (24) | 23.7 (16) | 63.2 (25) | 0.90 (3) | 68.7 (25) | 7.7 (8) |

TABLE 2-continued

Examples 11-13 and Comparative Examples 4-6

| | Example | | | | | |
|---|---|---|---|---|---|---|
| | 11 | CE4 | 12 | CE5 | 13 | CE6 |
| Flowability Index | 55 | 38 | 47 | 0.21 | 65 | 21.5 |
| Floodability Index | 88 | 66.5 | 83 | 18 | 84 | 32 |
| Total Index | 143 | 104.5 | 130 | 39 | 149 | 53.5 |

TABLE 3

Examples 14-19

| | Example | | | | | |
|---|---|---|---|---|---|---|
| | 14 | 15 | 16 | 17 | 18 | 19 |
| Powder from Example | 4 | 5 | 6 | 7 | 8 | 9 |
| Angle of Repose (Index) | 24.9 (25) | 30.5 (22) | 45.1 (15) | 35.7 (19.5) | 31.7 (21) | 51.8 (12) |
| Angle of Fall (Index) | 15.4 (24) | 18.4 (24) | 30.6 (17.5) | 15.2 (24) | 18.4 (24) | 39.8 (15) |
| Angle of Difference (Index) | 9.5 (10) | 10.2 (10) | 14.5 (15) | 20.5 (18) | 13.3 (12) | 12 (12) |
| Loose Bulk Density | 0.822 | 0.694 | 0.442 | 0.706 | 0.801 | 0.408 |
| Packed Bulk Density | 1.187 | 1.166 | 0.965 | 1.149 | 1.237 | 0.857 |
| Compressibility (Index) | 30.7 (10) | 40.4 (2) | 54.1 (0) | 38.5 (2) | 35.2 (7) | 52.3 (0) |
| Cohesiveness (Index) | 16.8 (12) | 21.4 (12) | 71.8 (2) | 17.0 (12) | 22.9 (0) | 64.7 (2) |
| Angle of Spatula (Index) | 60.2 (15) | 71.2 (12) | 13.7 (7) | 69.8 (12) | 70.9 (12) | 27.7 (7) |
| Dispersibility (Index) | 75.9 (25) | 56.0 (25) | 13.7 (12) | 19.3 (14.5) | 70.9 (25) | 27.7 (17.5) |
| Flowability Index | 62 | 50 | 24 | 45.5 | 40 | 21 |
| Floodability Index | 84 | 80 | 47 | 74.5 | 77 | 44.5 |
| Total Index | 146 | 130 | 71 | 120 | 117 | 65.5 |

Example 20 and Comparative Example 7

In Example 20, the mixture of albuterol sulfate and surface-modified nanoparticles of Example 10 was placed in the reservoir of a TURBUHALER dry powder inhaler device ("DPI" device, manufactured by Astra Pharmaceuticals, London, United Kingdom). In Comparative Example 7, the reservoir of another TURBUHALER dry powder inhaler device was charged with albuterol sulfate powder. The delivery characteristics of each of the dry powders from the dry powder inhaler devices were then evaluated using a Model 160 Marple Miller Impactor ("MMI") coupled with a USP throat (United States Pharmacopeia, USP 24 <601> Aerosols, Metered Dose Inhalers, and Dry Powder Inhalers, FIG. 4) and a volumetric flow rate of 60 liters per minute. A suitable coupler was affixed to the USP induction port to provide an air-tight seal between the DPI device and the induction port. For all testing, the stage cups of the MMI were coated with a surfactant to prevent particle bounce and re-entrainment. For each test, five doses were actuated from the DPI, one every fifteen seconds, holding the DPI in place for five seconds each actuation. After the last actuation, the DPI was held in place for five seconds and was then removed. The vacuum source was then left on for an additional 15 seconds before being turned off.

The amount of drug collected on each component of the MMI testing apparatus was determined by rinsing the component with a measured volume of an appropriate solvent and subjecting the rinsed material to HPLC analysis to determine albuterol sulfate concentration. Data that was returned from HPLC analysis was analyzed to determine the average amount of drug collected per delivered dose. The resulting mass values were then normalized to the fraction of delivered dose collected in each individual component of the testing assembly.

Using the individual component values, the amount of throat deposition, the respirable mass, and the respirable fraction was calculated for each device. Throat deposition is defined as the percent of the total delivered dose that deposits in the USP throat. Respirable mass is defined as the percentage of the total delivered dose that is measured to be smaller than the respirable limit of 4.7 micrometers in aerodynamic diameter. Respirable fraction is defined as the percentage of a delivered dose that reaches the entry of the throat and is smaller than the respirable limit. When using the MMI, respirable mass is collected in cups 2, 3, 4, and on the filter. Mass collected in the throat and cups 0 and 1 are considered non-respirable.

In Example 20, the device delivered 199 micrograms of powder per actuation and it was determined that 54% of the albuterol sulfate particles had an aerodynamic diameter less than 4.7 microns. In Comparative Example 7, the device delivered 68 micrograms per actuation and it was determined that 50% of the albuterol sulfate particles had an aerodynamic diameter less than 4.7 microns.

Examples 21-23

A stock dispersion of surface-modified nanoparticles (5 nm size, isooctyl/methyl surface modified) with a concentration of 0.005 g/mL was prepared by adding surface-modified nanoparticles (1.0 g) to a 200 mL volumetric flask and filling the remainder of the volume with heptane. A stir bar was placed in the flask and the mixture was stirred on a stir plate until the nanoparticles became fully dispersed based on visual appearance. Drug powder (5.0 g of albuterol base, flunisolide hemihydrate, and pirbuterol acetate, respectively) and stock nano-particle dispersion (10 mL) were added to a round bottom flask (1.0 L). Heptane was then added to the flask to bring the total volume to approximately 200 mL. The flask was sealed with a rubber stopper and the mixture was deagglomerated by sonication and hand swirling for approximately 3 to 5 minutes and until no agglomerated material could be seen sticking on the sides of the flask. The flask was then placed onto a rotary evaporator to remove the solvent. The rotary evaporator was set to a nominal temperature of 50° C. and operated under vacuum. After removal of all the solvent, the remaining powder was caked on the flask sides. The flask was then placed in a vacuum oven at 45° C. for approximately 1 hour to further remove any residual solvent. A stiff bristle brush was used to remove the caked powder from the walls of the flask and the powder was subsequently forced through a 400 mesh sieve to break up the agglomerated material. The sieved material was then collected and placed in a container for later use. The modified drug powder composition had a nominal concentration of surface-modified nanoparticles of 1.0 percent.

Delivery of the modified albuterol base powder from an Aerolizer® DPI device was evaluated using a Model 3321 Aerodynamic Particle Sizer Spectrometer™ (APS, TSI Inc., Shoreview, Minn.) coupled to a Model 3306 Impactor Inlet (TSI Inc., Shoreview, Minn.). The 3306 Impactor used the USP Inlet and was operated at an airflow velocity of 28.3 µm. The USP Inlet was coated with a thin layer of ethylene oxide/propylene oxide block copolymer surfactant (Pluronic® L-10 available from BASF Co., Florham Park, N.J.) in order to minimize particle bounce.

A commercially available Aerolizer® DPI device (from a Foradil® Aerolizer® product, available from Schering Plough Co.) was used to deliver the powder from Shionogi Quali-V® (hypromellose, also known as hydroxypropyl methylcellulose) capsules (Shionogi Qualicaps, Madrid, Spain). An Aerolizer® DPI device containing an empty capsule was coupled to the USP inlet and the APS Aerosol Pressure prop on the Model 3306 Impactor Inlet was adjusted to 0.3 inches of water per manufacturer calibration instructions. The Aerolizer® DPI device was then removed from the coupler, but the coupler was left attached to the USP Inlet. The opening of the coupler (that the Aerolizer® is inserted into) was partially restricted in order to maintain the 0.3 inches of water APS Aerosol Pressure prop when the Aerolizer® DPI device was not present.

The APS sampling time was set to 10 seconds. Approximately 5 mg of powder was loaded into a capsule and placed into the Aerolizer® DPI device. The capsule was punctured immediately prior to testing using the piercing mechanism of the Aerolizer® DPI device. The APS sampling was then started without the device in place. After five seconds of sampling, the coupler restriction was removed and the Aerolizer® DPI device with loaded capsule was immediately inserted into the opening in the coupler in order to deliver the drug from the DPI. The APS measured the total concentration of the powder from the sample, as shown in Table 4. The concentration of powder with aerodynamic diameters less than approximately 4.7 microns was determined from the APS measurement and is representative of particles likely to reach the deep lung of a patient. The results below are an average of three measurements for each powder type. Results are shown for the modified drug powder composition containing 1.0% surface-modified nanoparticles, as well as comparative examples ('CE') with unmodified drug powders.

TABLE 4

Examples 21-23 and Comparative Examples 8-10

| Example | Drug | Wt % Nano-particles | Concentration (mg/m$^3$) of particles <4.7 µm |
|---|---|---|---|
| 21 | Albuterol base | 1% | 0.756 |
| CE8 | Albuterol base | — | 0.553 |
| 22 | Flunisolide hemihydrate | 1% | 0.503 |
| CE9 | Flunisolide hemihydrate | — | 0.348 |
| 23 | Pirbuterol acetate | 1% | 0.456 |
| CE10 | Pirbuterol acetate | — | 0.327 |

Examples 24-26 and Comparative Example CE11

The surface-modified nanoparticles were added to glass bubbles (available from 3M Company under the trade designation "S60HS Glass Bubbles") to achieve the weight % listed in Table 5. Comparative Example CE11 used glass bubbles (available from 3M Company under the trade designation "S60HS Glass Bubbles") only. The resulting physical characteristics for Examples 24-26 and Comparative Example CE11 are listed in Table 6.

TABLE 5

Examples 24-26 and Comparative Example CE11

| Example | Nanoparticle Size | Surface Modification | Wt % Nanoparticles | Powder |
|---|---|---|---|---|
| CE11 | — | — | — | bubbles |
| 24 | 5 nm | isooctyl | 0.5% | bubbles |
| 25 | 5 nm | isooctyl | 0.2% | bubbles |
| 26 | 5 nm | isooctyl | 0.1% | bubbles |

TABLE 6

Examples 24-26 and Comparative Example CE11

| | Example | | | |
|---|---|---|---|---|
| | CE11 | 24 | 25 | 26 |
| Angle of Repose (Index) | 55.1 (10) | 37.6 (18) | 36.4 (19.5) | 49.1 (12) |
| Angle of Fall (Index) | 51.5 (8) | 33.7 (16) | 27.6 (18) | 47.4 (12) |
| Angle of Difference (Index) | 3.6 (3) | 3.9 (3) | 8.8 (9.5) | 1.7 (3) |
| Loose Bulk Density | 0.069 | 0.247 | 0.195 | 0.171 |
| Packed Bulk Density | 0.210 | 0.331 | 0.327 | 0.314 |
| Compressibility (Index) | 65.7 (0) | 25.4 (15) | 40.4 (2) | 45.5 (0) |
| Cohesiveness (Index) | 50.0 (7) | 4.6 (15) | 4.5 (15) | 4.3 (15) |
| Angle of Spatula (Index) | 50.3 (16) | 56.4 (18) | 50.1 (16) | 52.8 (16) |

TABLE 6-continued

Examples 24-26 and Comparative Example CE11

| | Example | | | |
|---|---|---|---|---|
| | CE11 | 24 | 25 | 26 |
| Dispersibility (Index) | 23.3 (16) | 72.2 (25) | 72.1 (25) | 70.4 (25) |
| Flowability Index | 33 | 66 | 52.5 | 43 |
| Floodability Index | 37 | 69 | 73.5 | 57 |
| Total Index | 70 | 135 | 126 | 100 |

Examples 27 and 28 and Comparative Example CE12

The surface-modified nanoparticles were added to ceramic microspheres (available from 3M Company under the trade designation "3M™ Ceramic Microspheres W-410") to achieve the weight % listed in Table 7. Comparative Example CE12 used ceramic microspheres (available from 3M Company under the trade designation "3M™ Ceramic Microspheres W-410" only. The resulting physical characteristics for Examples 27 and 28 and Comparative Example CE12 are listed in Table 8.

TABLE 7

Examples 27 and 28 and Comparative Example CE12

| Example | Nanoparticle Size | Surface Modification | Wt % Nanoparticles | Powder |
|---|---|---|---|---|
| CE12 | — | — | — | Ceramic microspheres |
| 27 | 5 nm | isooctyl | 2.0% | Ceramic microspheres |
| 28 | 5 nm | isooctyl | 0.4% | Ceramic microspheres |

TABLE 8

Examples 27 and 28 and Comparative Example CE12

| | Example | | |
|---|---|---|---|
| | CE12 | 27 | 28 |
| Angle of Repose (Index) | 50.5 (12) | 48.5 (12) | 48.3 (12) |
| Angle of Fall (Index) | 36.8 (16) | 36.0 (16) | 39.2 (16) |
| Angle of Difference (Index) | 13.7 (14.5) | 12.5 (12) | 9.1 (9.5) |
| Loose Bulk Density | 0.458 | 0.555 | 0.516 |
| Packed Bulk Density | 1.035 | 1.097 | 1.097 |
| Compressibility (Index) | 55.7 (0) | 49.4 (0) | 53.0 (0) |
| Cohesiveness (Index) | 59.9 (2) | 12.2 (12) | 43.8 (7) |
| Angle of Spatula (Index) | 55.2 (16) | 60 (15) | 57.3 (16) |
| Dispersibility (Index) | 27.9 (17.5) | 43.8 (24) | 26 (16) |
| Flowability Index | 30 | 39 | 35 |
| Floodability Index | 56 | 67 | 53.5 |
| Total Index | 86 | 106 | 88.5 |

Various modifications and alterations of this invention will be apparent to those skilled in the art without departing from the scope and spirit of this invention, and it should be understood that this invention is not limited to the illustrative embodiments set forth herein.

We claim:

1. A flowable powder composition comprising at least one bulk solid material in the form of a powder and non-aggregated surface-modified nanoparticles, wherein the average particle size of the nanoparticles is less than 100 nm, wherein the surface-modified nanoparticles comprise a surface-modifying group selected from the group consisting of silanes, organic acids, organic bases, alcohols, and combinations thereof, and wherein the surface-modified nanoparticles are present in the composition in an amount that is at least sufficient to improve the flowability or floodability of the bulk solid material relative to the bulk solid material free of surface-modified nanoparticles.

2. The composition of claim 1, wherein the bulk solid material contains one or more pharmaceutically active ingredients.

3. The composition of claim 1, wherein the powder comprises shaped particles.

4. The composition of claim 1, wherein the bulk solid material comprises particles having a median particle size diameter of less than 200 micrometers.

5. The composition of claim 1, wherein the amount of surface-modified nanoparticles is from 0.001 to 20 percent by weight of the composition.

6. The composition of claim 1, wherein the floodability is improved by at least 5 percent.

7. The composition of claim 1, wherein the surface-modified nanoparticles comprise a core and the core comprises an inorganic material selected from the group consisting of: silicas, calcium phosphates, iron oxides, zinc oxides, zirconia and alumina compounds.

8. The composition of claim 7, wherein the inorganic material is silica and wherein the surface-modifying agent is a silane.

9. The composition of claim 8, wherein the surface-modifying agent is selected from the group consisting of isooctyltrimethoxysilane, methyltrimethoxysilane, octadecyltrimethoxysilane, and combinations thereof.

10. The composition of claim 1, wherein the surface-modified nanoparticles comprise a core and the core comprises an organic material.

11. A flowable powder composition comprising a mixture of at least one bulk solid material in the form of a powder and non-aggregated surface-modified nanoparticles, wherein the average particle size of the nanoparticles is less than 100 nm, wherein the surface-modified nanoparticles comprise a surface-modifying group selected from the group consisting of silanes, organic acids, organic bases, alcohols, and combinations thereof, and wherein the surface-modified nanoparticles are present in the mixture in an amount at least sufficient to impart to the composition free flowability.

12. The composition of claim 11, wherein the bulk solid material is selected from the group consisting of a pharmaceutically active ingredient, a polymer, a glass, a ceramic bubble, a ceramic microsphere, and combinations of two or more of the foregoing.

13. The composition of claim 11, wherein the amount of surface-modified nanoparticles is from 0.001 to 20 percent by weight of the composition.

14. The composition of claim 1, wherein the bulk solid material contains one or more pharmaceutically active ingredients.

15. The composition of claim 1, wherein the average particle size of the nanoparticles is less than 50 nm.

16. The composition of claim 1, wherein the average particle size of the nanoparticles is less than 20 nm.

17. The composition of claim 1, wherein the average particle size of the nanoparticles is less than 10 nm.

18. The composition of claim 1 where the amount of surface-modified nanoparticles is from 0.001 to 10 percent by weight of the composition.

19. The composition of claim 1 where the amount of surface-modified nanoparticles is from 0.001 to 1 percent by weight of the composition.

20. The composition of claim 1 where the amount of surface-modified nanoparticles is from 0.001 to 0.01 percent by weight of the composition.

21. A method of making a flowable powder composition comprising mixing bulk solid material and non-aggregated surface-modified nanoparticles in a liquid and then removing the liquid, wherein the surface-modified nanoparticles are modified with a surface-modifying agent selected from the group consisting of silanes, organic acids, organic bases, alcohols, and combinations thereof.

22. The method of claim 21, wherein the bulk solid material is insoluble in the liquid.

23. The method of claim 21, wherein the surface-modified nanoparticles are dispersible in the liquid.

24. A method of delivering medicament to the lungs of a mammal by administering a therapeutic amount of a dry powder composition comprising pharmaceutically active ingredient and non-aggregated surface-modified nanoparticles, wherein the surface-modified nanoparticles are modified with a surface-modifying agent selected from the group consisting of silanes, organic acids, organic bases, alcohols, and combinations thereof.

25. The method of claim 24, wherein administration of the medicament is accomplished using a dry powder inhaler.

26. A dry powder inhalation device comprising a mouthpiece, a powder containment system and a powder composition comprising a mixture of at least one bulk solid material in the form of a powder and non-aggregated surface-modified nanoparticles, where the bulk solid material comprises at least one pharmaceutically active ingredient, and wherein the surface-modified nanoparticles comprise a surface-modifying group selected from the group consisting of silanes, organic acids, organic bases, alcohols, and combinations thereof.

27. The dry powder inhalation device of claim 26, wherein the pharmaceutically active ingredient is selected from the group consisting of steroids, beta-agonists, bronchodilators and anti-inflammatory preparations.

* * * * *

UNITED STATES PATENT AND TRADEMARK OFFICE
CERTIFICATE OF CORRECTION

| | | |
|---|---|---|
| PATENT NO. | : 8,062,670 B2 | |
| APPLICATION NO. | : 11/995845 | |
| DATED | : November 22, 2011 | |
| INVENTOR(S) | : Jimmie R Baran, Jr. | |

It is certified that error appears in the above-identified patent and that said Letters Patent is hereby corrected as shown below:

Column 1
Line 46, delete "(m," and insert -- (in, --, therefor.

Column 7
Line 65, delete "steric" and insert -- stearic --, therefor.

Column 8
Line 2, delete "steric" and insert -- stearic --, therefor.
Line 3, delete "steroyl" and insert -- stearoyl --, therefor.

Column 9
Line 29, delete "100 μm." and insert -- 100 nm. --, therefor.

Column 10
Line 10, delete "33M" and insert -- 3M™ --, therefor.

Column 12
Line 45, delete "and or" and insert -- and/or --, therefor.

Column 14
Line 39, delete "Carry" and insert -- Carr --, therefor.

Column 17
Line 25, delete "μm." and insert -- lpm. --, therefor.
Line 37, delete "prop" and insert -- Drop --, therefor.
Line 43, delete "prop" and insert -- Drop --, therefor.

Column 20
Line 61, in Claim 11, after "amount" insert -- of --.

Signed and Sealed this
Seventh Day of February, 2012

David J. Kappos
*Director of the United States Patent and Trademark Office*